(12) United States Patent
Giese (10) Patent No.: US 8,465,748 B2
(45) Date of Patent: Jun. 18, 2013

(54) VACCINE COMPOSITIONS AND METHODS CONTAINING AN IMMUNOGEN DERIVED FROM EQUINE ARTERITIS VIRUS

(76) Inventor: Matthias Giese, Heidelberg (DE)

( * ) Notice: Subject to any disclaimer, the term of this patent is extended or adjusted under 35 U.S.C. 154(b) by 467 days.

(21) Appl. No.: 12/730,618

(22) Filed: Mar. 24, 2010

(65) Prior Publication Data

US 2010/0247624 A1     Sep. 30, 2010

Related U.S. Application Data

(60) Provisional application No. 61/211,435, filed on Mar. 30, 2009.

(51) Int. Cl.
*A61K 39/12* (2006.01)
*C12N 15/00* (2006.01)
*C07H 21/02* (2006.01)
*C07H 21/04* (2006.01)

(52) U.S. Cl.
USPC ............... 424/204.1; 424/218.1; 424/199.1; 435/320.1; 536/23.1; 536/23.7; 536/23.72

(58) Field of Classification Search
None
See application file for complete search history.

(56) References Cited

PUBLICATIONS

Giese et al. Stable and Long-Lasting Immune Response in Horses after DNA Vaccination against Equine Arteritis Virus. Virus Genes 2002, vol. 25, No. 2, pp. 159-167.*
Krieg et al. The role of CpG dinucleotides in DNA vaccines. Trends in Microbiology, Jan. 1998, vol. 6, No. 1, p. 23-27.*

* cited by examiner

*Primary Examiner* — Louise Humphrey
(74) *Attorney, Agent, or Firm* — Stacey J. Farmer; Grund IP Group

(57) ABSTRACT

The present invention relates to vaccine compositions comprising a nucleic acid encoded by an equine arterivirus virus (EAV) open reading frame (ORF) 2 nucleic acid, and a nucleic vector comprising said EAV ORF 2. The invention further relates to the methods and kits encompassing the use of EAV ORF 2 containing vaccine compositions and nucleic acid vectors for the prevention and/or treatment of EAV infections.

15 Claims, 3 Drawing Sheets

FIGURE 1:

Schematic diagram of the genomic organization and transcriptional strategy of the family *Arteriviridae*.

FIGURE 2:

Cytotoxic T-cell lymphocyte (CTL) response observed for Horse 1 (Maisje).

FIGURE 3:

Cytotoxic T-cell lymphocyte (CTL) response observed for Horse 2 (Rudi)

SEQUENCE LISTING

<160> NUMBER OF SEQ ID NOS: 2

<210> SEQ ID NO 1
<211> LENGTH: 757
<212> TYPE: DNA
<213> ORGANISM: Artificial Sequence
<220> FEATURE:
<223> OTHER INFORMATION: EAV ORF 2

<400> SEQUENCE: 1

```
atgggcttag tgtggtcact gatttcaaat tctattcaga ctattattgc tgattttgct      60
atttctgtga ttgatgcagc gctttctctt ctcatgctac ttgcattggc tgttgttact     120
```

```
gtgtttctttt tctggctcat tgttgccatc ggccgcagct tggtggcgcg gtgttcacga    180
ggtgcgcgtt acagacctgt ttaaggattt gcagtgcgac aacctgcgcg cgaaagatgc    240
cttcccgagt ctgggatatg ctctgtcgat tggccagtcg aggctatcgt atatgctgca    300
ggattggttg cttgctgcgc accgcaagga agttatgcct tccaatatca tgcctatgcc    360
cggtcttact cctgattgct ttgaccatct ggagtcttct agctatgctc catttatcaa    420
tgcctatcgg caggcaattt tgagtcaata cccacaagag ctccagctcg aagccatcaa    480
ctgtaaattg cttgctgtgg ttgcaccggc attgtatcat aattaccatc tagccaattt    540
gaccggaccg gccacatggg tcgtgcctac agtgggccag ttgcactatt atgcttcttc    600
ctctattttt gcttcatctg tggaagtgtt ggcagcaata atactactat ttgcatgcat    660
accactagtg acacgagtgt acatctcttt tacgcggcta atgtcacctt cccgtcgcac    720
ttccagcggc actttgccgc ggcgcaagat tttgtag                              757

<210> SEQ ID NO 2
<211> LENGTH: 684
<212> TYPE: DNA
<213> ORGANISM: Artificial Sequence
<220> FEATURE:
<223> OTHER INFORMATION: EAV ORF 2b

<400> SEQUENCE: 2
tgctatttct gtgattgatg cagcgctttt ctttctcatg ctacttgcat tggctgttgt     60
tactgtgttt cttttctggc tcattgttgc catcggccgc agcttggtgg cgcggtgttc    120
acgaggtgcg cgttacagac ctgtttaagg atttgcagtg cgacaacctg cgcgcgaaag    180
atgccttccc gagtctggga tatgctctgt cgattggcca gtcgaggcta tcgtatatgc    240
tgcaggattg gttgcttgct gcgcaccgca aggaagttat gccttccaat atcatgccta    300
tgcccggtct tactcctgat tgctttgacc atctggagtc ttctagctat gctccattta    360
tcaatgccta tcggcaggca attttgagtc aatacccaca agagctccag ctcgaagcca    420
tcaactgtaa attgcttgct gtggttgcac cggcattgta tcataattac catctagcca    480
atttgaccgg accggccaca tgggtcgtgc ctacagtggg ccagttgcac tattatgctt    540
cttcctctat ttttgcttca tctgtggaag tgttggcagc aataatacta ctatttgcat    600
gcataccact agtgacacga gtgtacatct cttttacgcg gctaatgtca ccttcccgtc    660
gcacttccag cggcactttg ccgc                                            684
```

VACCINE COMPOSITIONS AND METHODS CONTAINING AN IMMUNOGEN DERIVED FROM EQUINE ARTERITIS VIRUS

TECHNICAL FIELD OF THE INVENTION

The present invention relates to vaccine compositions which provide protection or therapeutic treatment from clinical symptoms and/or infections caused by equine arteritis virus (EAV). In particular, the invention relates to vaccine compositions comprising a nucleic acid encoded by EAV including an open reading frame (ORF) 2 nucleic acid sequence, and/or a nucleic vector comprising EAV ORF 2. The invention further relates to the methods and kits encompassing the use of EAV ORF 2 containing vaccine compositions and nucleic acid vectors for the prevention and/or treatment of EAV infections.

BACKGROUND OF THE INVENTION

Equine arteritis virus (EAV) is a highly contagious virus that is spread via the respiratory or reproductive tract and causes persistent infections in horses and donkeys that are either asymptomatic or alternatively, quite severe like in those animals experiencing hemorrhagic fever or even miscarriages. EAV is a member of the Arteriviridae virus family, which also includes the lactate dehydrogenase-elevating virus (LDV), porcine reproductive and respiratory syndrome virus (PRRSV), and simian haemorrhagic fever virus (SHFV).

Figure 1:
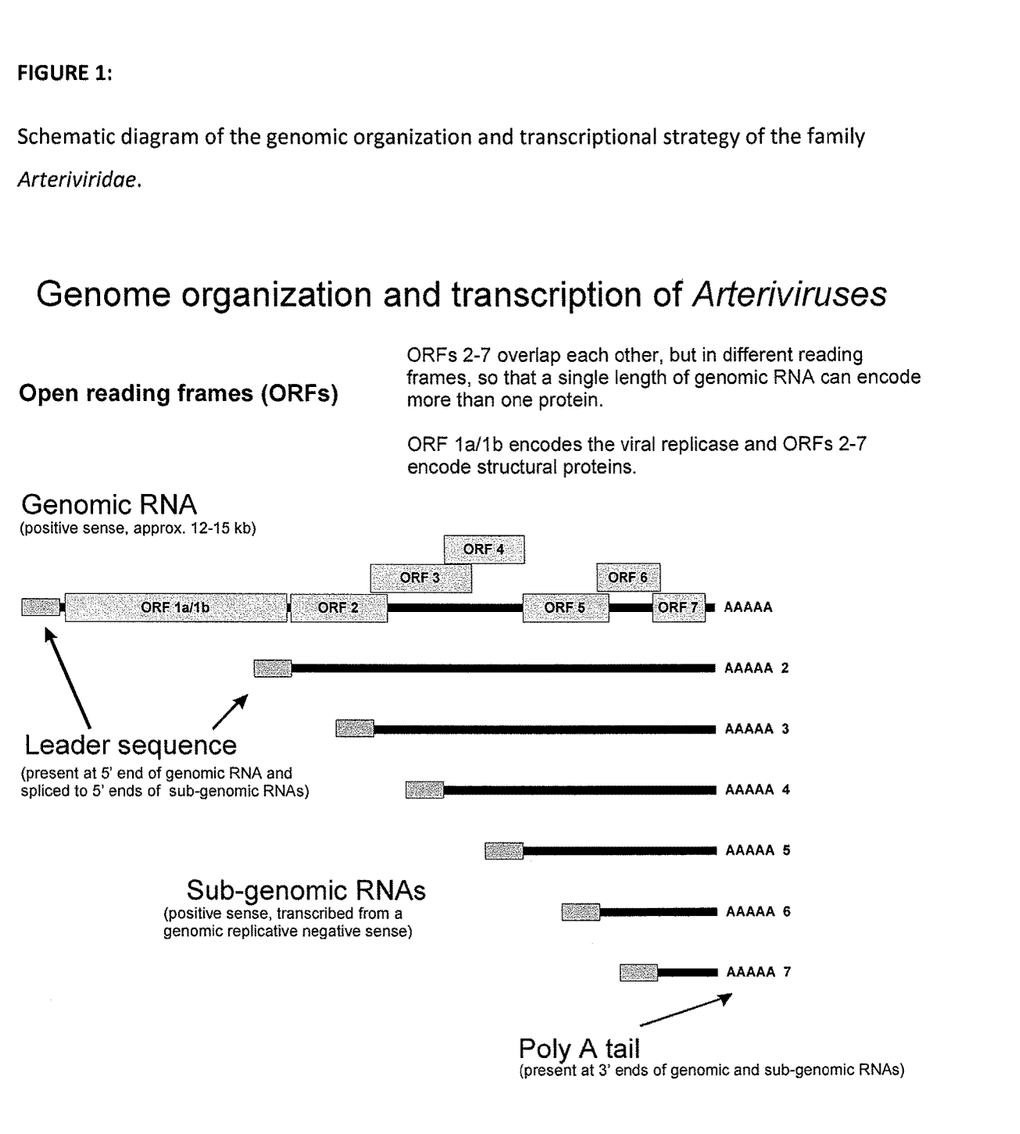
FIG. 1
Schematic diagram of the genomic organization and transcriptional strategy of the family Arteriviridae.

The biological and biophysical properties of EAV have frequently been the subject of experimental investigation, together with efforts to characterize EAV's viral pathogenesis and cell virus interactions. An overview of the genomic organization and transcriptional strategy of Arteriviruses is shown in FIG. 1.

EAV is characterized by a small (typically 60-65 nm in diameter) enveloped particle and has a 49S RNA genome that is a single-stranded, non-segmented, capped and polyadenylated message-sense RNA (12687 nucleotides; see den Boon et al., 1991, Equine arteritis virus is not a togavirus but belongs to the corona-virus-like superfamily. J. Virol. 65, 2910-2920; GenBank accession number: X53459).

The EAV genome is particularly infectious and contains at least eight open reading frames (ORF) including ORFs 1a, 1b, 2, 3, 4, 5, 6, and 7. The two largest viral ORFs (ORF 1a and ORF 1b) have been shown to encode the viral replicase (den Boon et al., 1991) and are located at the 5'-end of the viral genome between nucleotide positions 1 and 9807. ORFs 2 to 7 are overlapping and are situated at the 3'-end of EAV genome. The EAV transcript contains an N-glycosylated major membrane protein ("$G_L$", 30-44 kDa gene product of ORF 5), an unglycosylated membrane protein ("M", 17 kDa gene product of ORF 6), and a phosphorylated nucleocapsid protein ("N", 14 kDa, gene product of ORF 7). Moreover, the gene products derivable from the ORF 2 sequence include an N-glycosylated minor membrane protein ("$G_S$", from ORF-2b) and an envelope protein ("E", from ORF-2a), whereby the latter protein was found to be conserved in all Arteriviruses (Snijder et al., 1999, Identification of a novel structural protein of arteriviruses. J. Virol. 73, 6335-6345).

An analysis of the genetic stability of EAV during horizontal and vertical transmission in an outbreak of EAV has revealed that the carrier stallion is the primary source of EAV genetic diversity (Balasuriya et al., 1999, Genetic stability of equine arteritis virus during horizontal and vertical transmission in an outbreak of equine viral arteritis. J. Gen. Virol. 80, 1949-1958). It is known that the infected carrier stallion is a critical natural reservoir of EAV. EAV infection is maintained in horse populations primarily because chronic carrier animals shed the EAV in their semen, thus transmitting the virus during the mating process; the outbreak of an EAV infection can be initiated by the horizontal aerosol transmission of specific viral variants present in the semen fluid. One study has shown that not only does the carrier stallion act as the critical natural reservoir of EAV, but also that the genetic diversity of EAV is generated during the course of persistent infection in the infected horses (Patton et al., 1999, Phylogenetic characterization of a highly attenuated strain of equine arteritis virus from the semen of a persistently infected standardbred stallion. Arch. Virol. 144, 817-827).

The EAV ORF 6 encoded M protein is often considered to be the predominant target of the humoral immune response of horses against EAV. In one study, an enzyme linked immunosorbent assay (ELISA) was chosen to assess this response, and thus no biological function could be specifically attributed to the ensuing antibody response following exposure to EAV (Niewiesk et al., 1993, Susceptibility to measles virus-induced encephalitis in mice correlates with impaired antigen presentation to cytotoxic T lymphocytes, J. Virol. 67(1): 75-81). This M protein, together with the EAV ORF 5 encoded large envelope glycoprotein ($G_L$), form the major EAV viral envelope protein, and are associated with each other via a heterodimer disulfide bridge.

Vaccination is a highly effective intervention useful for controlling infectious diseases. Immunization with a naked DNA sequence offers an attractive, relatively inexpensive and powerful vaccination approach. By using a eukaryotic expression vector harboring the DNA nucleic sequence of a specific antigenic determinant, live-attenuated, killed or peptide vaccines, it is possible to circumvent many of the undesirable side-effects associated with conventional vaccines. The endogenous production of antigen by the host cell transcription machinery mimics aspects of live attenuated vaccines without the associated potential risk of recombination with or reversion to wild-type virus. Furthermore, distinction between vaccine and wild-type pathogen may be difficult and time-consuming, since there are typically no marker gene(s) incorporated into live-attenuated vaccines, which is of particular concern in the field of veterinary medicine.

Immunization with plasmid DNA expressing foreign antigens may provoke both a cellular and humoral immune response, which provides optimal protection against most virally caused infectious diseases. Cytotoxic T-lymphocyte ("CTL") activity is responsible for the elimination of infected cells, while antibodies bind to free virus to mediate lysis of infected cells. Viruses can, however, surreptitiously evade attack by the immune system and may establish persistent infections. Such viral persistence can result from several mechanisms, including high genetic variability of viral genomes, interference with cellular functions or depletion of subsets of immunocompetent cells.

Until now, attempts to develop a recombinant EAV vaccine therapy have been focused on the use of the EAV-derived M (ORF 6) and $GP_L$ (ORF 5) proteins, since: these proteins represent important targets for inducing a potent humoral immune response, are predominantly expressed on the viral outer membrane, and quantities of up to 30% of the EAV viral genome are usual.

One set of experiments has shown that an EAV vaccine composition consisting of the combination of EAV ORFs 2, 5, and 7 together, could successfully induce a stable and long-lasting immune response (Giese et al., 2002, Stable and Long-Lasting Immune Response in Horses after DNA Vaccination against Equine Arteritis Virus, Virus Genes, 25(2):159-67). The use of all three of these antigens in a combination vaccine (ORF 2: minor glycoprotein $GP_s$; ORF 5: large envelope glycoprotein $GP_L$; and ORF 7: nucleocapsid protein N) significantly stimulated cellular immunity in an antigen specific manner. While the EAV ORF 5 encoded viral membrane protein has been shown to be a powerful immunogen promoting humoral immunity; and the ORF 7 encoded viral capsid protein provokes a powerful cytotoxic response; the ORF 2 protein was included in the above EAV vaccine combination merely because it is highly conserved in the Arterivirus family and was thought to act as a stable back-up immunogen to the relatively unstable ORF 5, which has a very high mutation rate, despite the fact that the EAV ORF genome contains an extremely low percentage of the ORF 2 nucleic acid sequence (e.g. 1-2%), and therefore was not expected to itself generate any kind of meaningful immune response within the EAV vaccine.

Significantly, the use of EAV ORF 2 individually, i.e. without the other EAV ORF sequences, has not been the subject of any known EAV diagnostic or vaccine therapies, because relatively little is understood about the immunogenicity of this viral envelope glycoprotein. Moreover, as noted above, the EAV ORF 2 encoded proteins comprise only about 1-2% of the entire EAV virus. This particularly low antigen concentration could explain the rather poor antigenic recognition of the ORF 2 antigen in at least one mouse B-cell model, where limited antibody response was shown (Chirnside et al., 1995, Equine arteritis virus-neutralizing antibody in the horse is induced by a determinant on the large envelope glycoprotein $G_L$, J. Gen. Virol. 76, 1989-1998). These observations may explain why, until now, the exclusive use of ORF 2 in a vaccine composition against EAV has not been pursued.

The prevalence and highly contagious nature of EAV underscores the importance of finding preventative and/or therapeutic measures against this virus in order to prevent disastrous economic consequences on horse farming worldwide. Moreover, the development of an efficient vaccine composition, and methods of use, is of particular importance since these efforts contemplate both the preventative and therapeutic aspects of this disease.

Therefore, there is a need for an effective and 'uncomplicated' (e.g. low concentrations of antigen, low cross-reactivity, highly potent) vaccine composition against EAV that is capable of preventing and/or treating an EAV-associated disease, and a method of applying such a composition to a preferably equine subject.

SUMMARY OF THE INVENTION

It is therefore an object of the invention to provide a vaccine composition that is protective against Arteriviridae infections in an animal, wherein said Arteriviridae comprises the viruses: equine arteritis virus (EAV), porcine reproductive and respiratory syndrome virus (PRRSV), and simian haemorrhagic fever virus (SHFV).

It is also an object of the invention to provide a vaccine composition that is protective against EAV infections and induces a cellular immune response, wherein said vaccine comprises a nucleic acid encoding an EAV open reading frame (ORF) 2, preferably the EAV ORF 2b sequence.

It is an additional object of the invention to provide a nucleic acid vector comprising a nucleic acid encoding an EAV sequence including open reading frame (ORF) 2, preferably the EAV ORF 2b sequence.

It is also an object of the invention to provide for methods for prevention and/or treatment of an EAV infection using such vaccine compositions and/or nucleic acid vectors.

The invention also relates to the a kit comprising a vaccine composition according to the invention including the EAV ORF 2 DNA molecule according to the invention, or one or several nucleic acid vector(s) described herein.

DETAILED DESCRIPTION OF THE INVENTION

As used herein and in the appended claims, the singular forms "a", "an", and "the" include plural reference unless the context clearly dictates otherwise. Thus, for example, reference to "a nucleic acid molecule" includes a plurality of such nucleic acid molecules, reference to the "vector" is a reference to one or more vectors and equivalents thereof known to those skilled in the art, and so forth. Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies as reported in the publications which may be useful in connection with the instant invention. Nothing herein is to be construed as an admission that the invention is not entitled to antedate these disclosures by virtue of prior invention.

The term "EAV" as used herein refers to all viruses belonging to species 'equine arteritis virus' of the family Arteriviridae.

A "fragment" according to the invention is any subunit of a DNA molecule (e.g. part of an EAV open reading frame (ORF)) of a longer DNA molecule (e.g. an entire EAV ORF) according to the invention, i.e. any subset, characterized in that it is encoded by a shorter nucleic acid molecule than disclosed which can still be transcribed into RNA. "Fragment" also relates to subsets of proteins, i.e. smaller proteins encoded by said DNA fragments. The expression is to be understood depending upon the context in which it is used.

A "functional variant" of the DNA molecule according to the invention or protein encoded thereby is a DNA molecule or protein which possesses a biological activity (either functional or structural) that is substantially similar to the DNA molecule or protein according to the invention. The term "functional variant" also includes "a fragment", "a functional variant", "a variant based on the degenerative nucleic acid code" or "a chemical derivative". A "functional variant" may carry one or several nucleic acid exchanges, deletions or insertions, which may account for up to 10% of the entire nucleic acid sequence. A functional variant at least partially retains its biological activity, such as an infectious clone or a vaccine strain, or can exhibit enhanced biological activity.

A "variant based on the degenerative nature of the genetic code" is a variant resulting from the fact that a certain amino acid may be encoded by more than one codon. A variant at least partially retains its biological activity, or can exhibit enhanced biological activity.

According to the invention, "mutation" means the replacement of a nucleotide by another (e.g. C for a T), or a "substitution" or any other mutation such as "deletion" or "insertion". "Deletion" means the removal of one or several nucleotides or amino acids, "Insertion" means the addition of one or several nucleotides or amino acids.

A "fusion molecule" may be a DNA molecule or protein according to the invention fused to, e.g. a reporter such as a radiolabel, a chemical molecule such as a fluorescent label or any other molecule known in the art.

As used herein, a "chemical derivative" according to the invention is a DNA molecule or protein according to the invention that is chemically modified or contains additional chemical moieties not normally included in the molecule. Such moieties may improve the molecule's solubility, absorption, biological half life or other like characteristics.

A molecule is "substantially similar" to another molecule if both molecules have substantially similar nucleotide sequences or biological activity. Thus, provided that two molecules possess a similar biological activity, they are considered variants as that term is used herein if the nucleotide sequence is not completely identical. Two molecules which have a similar nucleotide sequence are considered variants as that term is used herein even if their biological activity is not identical.

The term "vaccine" as used herein refers to a pharmaceutical composition comprising at least one immunologically active component that induces an immunological response in an animal and possibly but not necessarily one or more additional components that enhance the immunological activity of said active component. A vaccine may additionally comprise further components typical to pharmaceutical compositions. The immunologically active component of a vaccine may comprise complete virus particles in either their original form or as attenuated particles in a "modified live vaccine" (MLV) or particles inactivated by appropriate methods in a "killed vaccine" (KV). The terms "vaccine" and "vaccine composition" are used interchangeably in the present invention.

In another embodiment, the immunologically active component of a vaccine may comprise appropriate elements of said organisms (subunit vaccines) whereby these elements are generated either by destroying the whole particle or the growth cultures containing such particles and optionally subsequent purification steps yielding the desired structure(s), or by synthetic processes including an appropriate manipulation by use of a suitable system based on, for example, bacteria, insects, mammalian or other species plus optionally subsequent isolation and purification procedures, or by induction of said synthetic processes in the animal needing a vaccine by direct incorporation of genetic material using suitable pharmaceutical compositions (polynucleotide vaccination). A vaccine may comprise one or simultaneously more than one of the elements described above.

"Vaccine" also refers to a vaccine for veterinary use and comprises antigenic substances and is administered for the purpose of inducing a specific and active immunity against a disease provoked by EAV. The EAV vaccine according to the invention confers active immunity that may be transferred passively via maternal antibodies against the immunogens it contains and in some cases, additionally against antigenically related organisms.

Additional components to enhance the immune response are constituents commonly referred to as adjuvants, including, for example, aluminium hydroxide, mineral or other oils or ancillary molecules added to the vaccine or generated by the body after the respective induction by such additional components, like but not restricted to interferons, interleukins or growth factors.

A "vaccine composition" essentially consists of one or more ingredients capable of modifying physiological e.g. immunological functions of the organism it is administered to, or of organisms living in or on the organism. The term includes, but is not restricted to antibiotics or antiparasitics, as well as other constituents commonly used to achieve certain other objectives like, but not limited to, processing traits, sterility, stability, feasibility to administer the composition via enteral or parenteral routes such as oral, intranasal, intravenous, intramuscular, subcutaneous, intradermal or other suitable route, tolerance after administration, controlled release properties.

There is a need for a vaccine capable of preventing or treating an EAV-associated disease, a need that has been met by the present invention, which provides a nucleic acid-based preventative and/or therapeutic vaccine composition against EAV-associated diseases.

Surprisingly, the nucleic acid-based EAV ORF 2 vaccine according to the invention provides, for the first time, a capability of not only generating a substantial humoral (antibody-based) response (see, e.g. EXAMPLE 1), but this vaccine can also induce a direct and sustainable cellular immune response in an equine subject. One cellular immune response, as shown in EXAMPLE 2, is protective against both horizontal and vertical EAV transmission in horses. Another unexpected finding was that a vaccine composition containing exclusively the EAV ORF 2 sequence, and no other EAV ORF sequence, was shown to be immunoprotective against EAV infection in horses at different stages of development (see, e.g. TABLE 4) (Barry and Johnston, 1997, Biological features of genetic immunization. Vaccine 15, 788-795).

In one embodiment, the invention concerns a vaccine composition that is protective against EAV infections in horse subjects, by inducing a cellular immune response, wherein the vaccine composition comprises an open reading frame nucleic acid (ORF) 2 sequence, preferably the ORF 2b sequence, and/or the polypeptide encoded thereby. This vaccine configuration is unforeseen to the skilled person working in this technical field, namely that a single EAV ORF sequence, namely ORF 2, could be therapeutically beneficial as a vaccine, in particular given the comparatively small presence of ORF 2 (e.g. 1-2%) relative to other ORFs within the entire EAV genome.

Thus, the present invention relates to a vaccine composition that is protective against viral invasion from the Arteriviridae family and induces a cellular immune response, comprising an EAV ORF 2 nucleic acid, optionally comprised in a nucleic acid vector and/or linked to regulatory nucleic acid elements. The vaccine may also include the polypeptide encoded by the EAV ORF 2 nucleic acid, and/or a nucleic acid encoding interleukin 2 (IL-2), such as equine IL-2, or a vector or expression vector comprising said nucleic acid encoding IL-2 (or the vector or expression vector comprising the IL-2 encoding nucleic acid) and/or a pharmaceutically acceptable carriers, adjuvants and/or excipients.

Unexpectedly, a vaccine comprising the EAV ORF 2 alone, preferably the ORF 2b EAV sequence, is particularly effective compared to a vaccine where the entire EAV cDNA transcript is used. ORF 2 as used herein refers to the entirety of the EAV ORF 2 nucleic acid that confers immunogenic activity. The ORF 2 nucleic acid sequence, in particular the ORF 2b sequence, encodes a minor glycoprotein known as $G_S$ (TABLE 2). As understood herein, a "polypeptide" and a "glycoprotein" as encoded by EAV ORF 2 are used synonymously. The "glycoprotein" encoded by the EAV ORF 2 also refers to fragments, functional variants, fusion molecules, chemical derivatives or glycosylation variants.

In a preferred embodiment, the vaccine composition according to the invention is protective against infections of the EAV infections in horses.

The invention encompasses vaccine compositions wherein said ORF 2, preferably ORF 2b, is present as fragments, functional variants or contains mutations as defined above.

The invention also relates to a vaccine composition, wherein said nucleic acid is cDNA.

In particular, the EAV ORF 2 nucleic acid may have the nucleic sequence of SEQ ID. NO:1, a fragment, functional variant, variant based on the degenerative nucleic acid code, fusion molecule or a chemical derivative thereof.

To prepare the nucleic acids according to the invention, the skilled person may consult the EXAMPLES of the present invention, and further apply known standard molecular biology methods which can be found e.g. in Sambrook et al. (1989) Molecular Cloning: A Laboratory Manual, $2^{nd}$ ed., Cold Spring Harbor Laboratory Press, Cold Spring Harbor, N.Y. and Bertram, S, and Gassen, H. G. (1991) Gentechnische Methoden, G. Fischer Verlag, Stuttgart, as applicable.

In one embodiment according to the invention, said vaccine composition includes a single nucleic acid vector comprising said ORF 2.

The invention further relates to a vaccine composition according to the invention, wherein said vector is an expression vector.

The invention further relates to a vaccine composition according to the invention, wherein said expression vector comprises a eukaryotic cis-acting transcription/translation sequence functionally linked to said ORF 2.

The invention further relates to a vaccine composition according to the invention, wherein said expression vector is selected from the group of pCR3.1, pcDNA3.1/His A, pcDNA3.1/His B, pcDNA3.1/His C, and pDisplay (pD), wherein these vectors are commercially available (e.g. Invitrogen, Chatsworth, Calif.).

The invention further relates to a vaccine composition according to the invention, further comprising the nucleic acid encoding interleukin 2 (IL-2), such as equine IL-2, or a vector or expression vector comprising said nucleic acid encoding IL-2.

The invention further relates to a vaccine composition according to the invention, further comprising a pharmaceutically acceptable carrier or excipient.

The invention further relates to a vaccine composition according to the invention, further comprising one or several adjuvants selected from the group of Muramyl Dipeptide (MDP), Montanide 720, Poly Inosine:Cytosine (Poly I:C) or plasmid DNA comprising unmethylated cytosine, guanine dinucleotide sequence motifs (CpG).

The invention relates to a vaccine according to the invention, wherein the adjuvants can be any of the compounds disclosed in Chapter 7 (pp 141-227) of "Vaccine Design, The Subunit and Adjuvant Approach" (eds. Powell, M. F. and Newman, M. J.) Pharmaceutical Biotechnology, Volume 6, Plenum Press (New York). Examples from this compendium include Muramyl Dipeptide (MDP) and Montanide 720. Molecules such as Poly Inosine:Cytosine (Poly I:C) or "immunostimulatory nucleic acid molecules" such as plasmid DNA containing CpG motifs can also be administered as adjuvants in combination with antigens encapsulated in microparticles. An "immunostimulatory nucleic acid molecule" refers to a nucleic acid molecule, which contains an unmethylated cytosine, guanine dinucleotide sequence (i.e. "CpG DNA" or DNA containing a cytosine followed by guanosine and linked by a phosphate bond) and stimulates (e.g. has a mitogenic effect on, or induces or increases cytokine expression by) a vertebrate lymphocyte. An immuno-stimulatory nucleic acid molecule can be double-stranded or single-stranded. Generally, double-stranded molecules are more stable in vivo, while single-stranded molecules have increased immune activity. The instant invention is based on the finding that certain "immuno-stimulatory nucleic acid molecules" containing unmethylated cytosine-guanine (CpG) dinucleotides activate lymphocytes in a subject and redirect a subject's immune response from a Th2 to a Th1 (e.g. by inducing monocytic cells and other cells to produce Th1 cytokines, including IL-12, IFN-gamma, and GM-CSF).

The invention further relates to a vaccine composition according to the invention, comprising an expression vector comprising ORF 2 of EAV, and optionally a carrier, excipients or adjuvants and an expression vector comprising the nucleic acid encoding IL-2, wherein the IL-2 is preferably equine IL-2. The nucleic acid encoding equine IL-2 can also be co-expressed on a vector as disclosed supra, and encoding said EAV ORF 2.

Suitable for targeted delivery of the vaccine composition according to the invention are colloidal dispersion systems or liposomes. One example of a targeted delivery system for the EAV ORF nucleic acid molecules according to the invention is said colloidal dispersion system. Colloidal dispersion systems include macromolecule complexes, nanocapsules, microspheres, beads, and lipid-based systems including oil-in-water emulsions, micelles, mixed micelles, and liposomes or liposome formulations. The preferred colloidal system of this invention is a liposome. Liposomes are artificial membrane vesicles which are useful as delivery vehicles in vitro and in vivo. These formulations may have net cationic, anionic or neutral charge characteristics are useful characteristics with in vitro, in vivo and ex vivo delivery methods. It has been shown that large unilamellar vesicles (LUV), which range in size from 0.2-4.0 μm can encapsulate a substantial percentage of an aqueous buffer containing large macromolecules. RNA, DNA and intact virions can be encapsulated within the aqueous interior and be delivered to cells in a biologically active form (Fraley and Papahadjopoulos, 1981, New generation liposomes: the engineering of an efficient vehicle for intracellular delivery of nucleic acids Trends in Biochemical Sciences Volume 6, 1981, pages 77-80). In addition to mammalian cells, liposomes have been used for delivery of polynucleotides in plant, yeast and bacterial cells. In order for a liposome to be an efficient gene transfer vehicle of EAV ORF 2 according to the invention, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino and Gould-Fogerite, 1988, Rotary dialysis: Its application to the preparation of large liposomes and large proteoliposomes (protein-lipid vesicles)

with high encapsulation efficiency and efficient reconstitution of membrane proteins, Analytical Biochemistry, Volume 148, Issue 1, July 1985, pages 15-25).

The liposome composition is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Thus, in a preferred embodiment, the vaccine according to the invention comprises any of the above-mentioned delivery systems.

The vaccine composition of the present invention may contain said recombinant vector as a naked "gene expression vector". This means that the construct is not associated with a delivery vehicle (e.g. liposomes, colloidal particles and the like). One of the principal advantages of naked DNA vectors is the lack of an unwanted immune response stimulated by the vector itself.

The invention further relates to a vaccine composition according to the invention, wherein the nucleic acid or nucleic acid vector or expression vector is encapsulated into liposomes. Preferably, in a vaccine composition according to the invention, the nucleic acid or nucleic acid vector or expression vector is encapsulated into cationic liposomes.

Several types of liposomal preparations may be used for encapsulation, including large multilamellar vesicles, small unilamellar vesicles, neutral, anionic liposomes or simple cationic amphiphiles. Most preferred are cationic liposomes.

These synthetic gene delivery systems are described by various terms:

The cationic lipid-mediated transfection has been also called liposome-mediated-transfection, cationic liposome-mediated transfection, lipofection, cytofection, amphifection, and lipid-mediated transfection. Similarly, the complexes that are produced when cationic lipids are mixed with DNA have been referred to as cytosomes, amphisomes, liposomes, nucleolipidic particles, cationic lipid-DNA complexes, lipid-DNA complexes, DNA-lipid complexes etc. A common nomenclature has been proposed: Lipoplex replaces all of the terms for cationic lipid-nucleic acid complexes (including DNA, RNA, or synthetic oligonucleotides) and lipofection means the nucleic acid delivery mediated by lipoplexes. Any of said gene delivery system may be used according to the invention.

The positive charge on cationic lipid molecules facilitates their association with negatively charged nucleic acid as well as with membrane phospholipids (negatively charged) what is the basis for the non-specific interaction of the complex.

The specific binding to the cell is mediated by use of specific ligands for cellular receptors. Cationic liposomes may deliver DNA either directly across the plasma membrane or via endosome compartment. Regardless of its exact entry point, much of the DNA does accumulate in the endosomes and is lost by the internal hydrolytic digestion within the endosomes. To protect the plasmid DNA several strategies may be used according to the invention. This includes the use of acidotropic, weak amines such as chloroquine, which presumably prevent DNA degradation by inhibiting endosomal acidification. But also viral fusion peptides or whole viruses may be included to disrupt endosomes or promote fusion of liposomes with endosomes and facilitate release of DNA into the cytoplasm. Such protection of the plasmid DNA is also a preferred embodiment of the invention.

The DNA concentration, the ratio of lipid reagent to DNA, the transfection time and the effect of serum are the most critical factors in each transfection.

Liposomes must be stable. In case of leakage they would undesirably and prematurely lose antigen and adjuvants.

Another embodiment relates to a vaccine composition according to the invention comprising 50 µg of individual nucleic acid vector, or preferred expression vector, and preferably for 3 injections per animal, i.e. 1000 µg of individual nucleic acid vector (or preferred expression vector) per vaccination, for example, if seven nucleic acid vectors (or preferred expression vectors) are used, then 1,000 mg per vaccination and animal (EXAMPLE 2).

In yet another embodiment, the invention relates to a nucleic acid vector comprising a nucleic acid encoding EAV ORF 2, wherein the nucleic acid is DNA.

In particular, the EAV ORF 2 nucleic acid may have the following nucleic sequence or a fragment, functional variant, variant based on the degenerative nucleic acid code, fusion molecule or a chemical derivative thereof of the nucleic acid sequence that is SEQ ID. NO:1.

A more preferred aspect of the invention is a nucleic acid vector according to the invention, wherein said nucleic acid vector is an expression vector.

Another aspect of the invention is a nucleic acid vector according to the invention, wherein said expression vector comprises a eukaryotic cis-acting transcription/translation sequence functionally linked to said ORF 2.

To accomplish expression, a wide variety of vectors have been developed and are commercially available which allow inducible (e.g., LacSwitch expression vectors, Stratagene, La Jolla, Calif.) or cognate (e.g., pcDNA3 vectors, Invitrogen, Chatsworth, Calif.) expression of EAV ORF nucleotide sequences under the regulation of an artificial promoter element. Such promoter elements are often derived from CMV of SV40 viral genes, although other strong promoter elements which are active in eukaryotic cells can also be employed to induce transcription of EAV ORF nucleotide sequences. Typically, these vectors also contain an artificial polyadenylation sequence and 3' UTR which can also be derived from exogenous viral gene sequences or from other eukaryotic genes. Furthermore, in some constructs, artificial, non-coding, spliceable introns and exons are included in the vector to enhance expression of the nucleotide sequence of interest (in this case, EAV ORF sequences). These expression systems are commonly available from commercial sources and are typified by vectors such as pcDNA3 and pZeoSV (Invitrogen, San Diego, Calif.). Numerous commercially-available as well as custom-designed expression vectors are available from commercial sources to allow expression of any desired EAV ORF transcript in more or less any desired cell type, either constitutively or after exposure to a certain exogenous, stimulus (e.g., withdrawal of tetracycline or exposure to IPTG).

Another aspect of the invention is a nucleic acid according to the invention, wherein said expression vector is selected from the group of pCR3.1, pcDNA3.1/His A, pcDNA3.1/His B, pcDNA3.1/His C, and pDisplay (pD).

Another embodiment of the invention is a method for the prevention and/or treatment of EAV infection in a horse, comprising (i) coating one or several nucleic acid or EAV DNA molecule(s) encoding ORF2 of EAV according to the invention, or one or several nucleic acid vector(s) according to the invention, onto carrier particles; (ii) accelerating the coated carrier particles into epidermal cells of the horse in vivo; (iii) inducing a protective or therapeutic immune response in said horse upon or after exposure to EAV; and (iv)

monitoring the reduction of EAV-associated symptoms or the reduction of horizontal or vertical transmission.

In a preferred method according to the invention, the carrier particles are gold.

Preferred vaccination schemes include: only one foundational (base) immunization without a booster; or a base immunization, followed by a first boost after 8-12 weeks; or a base immunization, a first boost after 8-12 weeks, and a second boost after 12 months.

The vaccine composition molecule(s) according to the invention, or one or several nucleic acid vector(s) as disclosed above, may be administered by any known route of administration: preferably orally, nasally, lingually, intravenously (i.v.), intradermally (i.d.), intraepidermally (by rubbing into the skin), intranasally, vaginally, subcutaneously (s.c.), or via an intramuscular (i.m.) route.

According to the invention, various vehicles for administration of the vaccine, molecule(s) according to the invention, or one or several nucleic acid vector(s) according to the invention may be used such as plasmid 'naked' DNA inoculation by needle, liposomes, gold beads, biodegradable nanoparticles, virus like particles (VLP), and/or aerosol.

Preferred modes of administration for the vaccine composition molecule(s) according to the invention, or one or several nucleic acid vector(s) according to the invention include: injection by needle, gene gun, encapsulated in liposomes or rubbing into the skin.

One preferred method of vaccination is the direct injection of plasmid DNA into the skeletal muscle. In this case, sustained immune responses are achieved in many cases without the need for subsequent booster applications.

Yet another important embodiment of the invention is a method for the prevention and/or treatment of EAV infection in a horse, comprising (i) injecting a vaccine composition according to the invention, or one or several nucleic acid or molecule(s) encoding ORF 2 of EAV and/or IL-2 according to the invention, or one or several nucleic acid vector(s) according to the invention into the muscular cells of the horse in vivo; and (ii) inducing a protective or therapeutic immune response in said horse upon or after exposure to EAV, and (iii) monitoring the reduction of EAV-associated symptoms or the reduction of horizontal or vertical transmission.

Preferably, said method may be carried out in a repeated fashion. An appropriate vaccination scheme may be preferably on day 0 (basic vaccination), 4 weeks after the basic vaccination and 8 weeks after the basic vaccination, as provided in EXAMPLE 2. Preferred doses include 1000 µg of individual nucleic acid vector or preferred expression vector and 3 inoculations per animal, of individual nucleic acid vector (or preferred expression vector) per vaccination.

Another embodiment of the invention relates to typical application of the disclosed vaccine composition, or nucleic acid vector(s), comprising a composition dosing of: low range 10-100 µg, preferably 50 µg, middle range 101-500 µg, preferably 200 µg, high range 501 µg-2000 µg, preferably 1000 µg. Again, the skilled person can readily determine the criteria for the most beneficial dose, which is known to depend on the chosen route of administration. For example, where the vaccine composition is applied with a gene gun, the vaccine is injected directly into Langerhans cells, thus very little of antigen escapes; when applied via i.m. injection, a higher vaccine dose is required.

Another vaccination scheme includes: only one foundational (base) immunization without a booster; or a base immunization, followed by a first boost after 8-12 weeks; or a base immunization, a first boost after 8-12 weeks, and a second boost after 12 months.

The invention also relates to a kit comprising a vaccine composition according to the invention and/or the EAV ORF 2 molecule according to the invention and/or one or several nucleic acid vector(s) according to the invention. The kit is conveniently ready-to-use for vaccination. The kit may further comprise other suitable containers, washing reagents and reaction buffers (which may vary in pH and magnesium concentrations), sterile water, liposomal preparations, transfection reagent such as DOTAP Liposomal (Roche) or Lipofectin, BME (Eagle's basal medium), ethanol, gold, spermidine, $CaCl_2$, carrier proteins and further compounds known to the skilled person.

The following examples serve to further illustrate the present invention; but the same should not be construed as limiting the scope of the disclosed invention.

EXAMPLES

Example 1

Neutralization Tests
Materials and Methods
Viruses and Cells

The EAV sequences used in this study was kindly provided by Professor H. Ludwig, Berlin and propagated on rabbit kidney cells (RK13, ATCC number CCL-37). The cell cultures were obtained from the American Type Culture Collection and propagated in Basal Medium Eagle (BME) supplemented with 10% fetal calf serum, 100 IE/penicillin G, 100 IE/ml streptomycin. Medium and serum were purchased from GibcoBRL (Eggenstein, Germany).

Production of EAV-Specific Antisera

Antiserum against EAV was induced in New Zealand white rabbit. The animal was inoculated subcutaneously with 0.5 ml purified EAV. Inoculation was repeated for four times. An exemplary experimental protocol is summarized in TABLE 1. The sensitivity of rabbit antisera was determined by Western blot analysis. It was found that the rabbit antiserum raised against EAV was able to recognize viral specific protein at a dilution of about 1:2000 and higher.

Preparation of Viral RNA

Virion RNA and total infected cell RNA was prepared from EAV-infected RK13 cell cultures at 12, 24, 36, and 48 hour p.i. using a guanidinium iso-thiocyanate/cesium chloride procedure based on the method previously described (Glišin et al., 1974, Ribonucleic acid isolated by cesium chloride centrifugation, Biochemistry 13, 2633-2637). Infected cells or virions from clarified infected cell culture supernatants were dissolved in a 4.0 M guanidinium thiocyanate (GTC) solution. Cellular DNA in the infected cell preparation was sheared by repeatedly passing the solution through a 23-gauge needle. CsCl and sarcosyl (30% aqueous solution) were added to the GTC preparation to final concentrations of 0.15 g/ml and 3.0%, respectively. In volumes of 8 ml, the preparation was transferred onto a 3 ml 5.7 M CsCl cushion and centrifuged at 29,000 rpm in a Beckman SW41 rotor for 24 h at 20° C. The supernatant was discarded and the RNA pellet was dissolved in RNase free $H_2O$ to a final concentration of about 10 µg/ml. RNA preparations were stored at −20° C. in 80% ethanol containing 100 mM sodium acetate. As an alternative, total RNA from EAV-infected cells was prepared using the RNeasy Mini Kit (Qiagen, Hilden, Germany) according to the instructions of the manufacturer.

First-Strand cDNA Synthesis

For each first-strand cDNA synthesis reaction approximately 0.5 µg of purified RNA were pelleted and dissolved in 10 µl RNase free $H_2O$ containing 20 U RNase inhibitor (Takara Shuzo Co., Ltd., Shiga, Japan). The reaction was prepared in 20 µl volumes using enzymes and reagents from the RNA LA PCR Kit Ver. 1.1 (Takara Shuzo Co., Ltd., Shiga, Japan) according to the instructions of the manufacturer. The reaction included 5 mM $MgCl_2$, 1 mM of each dNTP, 10 pmol of a specific reverse oligonucleotide primer, and 5 U AMV reverse transcriptase XL. The reaction was incubated in an automated temperature cycling reactor (Genius, Techne, Cambridge, UK) for 2 min at 60° C. followed by 15 min at 50° C. Then the temperature was gradually lowered to 42° C. at a speed of 1° C./min. As a final step, the reaction was incubated for 2 min at 80° C. and rapidly cooled to 4° C. RNase free $H_2O$ was added to the reaction products to obtain a final volume of 100 µl. The first-strand cDNA stocks were stored at −20° C.

Oligonucleotides and Polymerase Chain Reaction (PCR)

Specific oligonucleotides were synthesized with an Oligo 1000M DNA Synthesizer (Beckman Instruments GmbH, München, Germany). Polymerase chain reaction (PCR) was performed in 100 µl volumes using TaKaRa LA Taq DNA polymerase (supplied with reaction buffer, Takara Shuzo Co., Ltd., Shiga, Japan). Each reaction contained 1.5-2.5 mM $MgCl_2$, 12.5 nmol of each dNTP (Boehringer Mannheim Biochemica, Mannheim, Germany), 50 pmol of each oligonucleotide primer, and 1 µl of a first-strand cDNA stock solution (see above). An improved PCR protocol was developed based on a combination of commonly used hot-start and touch-down procedures. Briefly, before adding the dNTP mixture and the DNA polymerase the samples were preheated for 5 min at 94° C. and rapidly cooled to 4° C. Then dNTPs and DNA polymerase were added at 4° C. and the reaction tubes were directly transferred to a preheated temperature cycling reactor (Genius, Techne, Cambridge, UK) at 94° C. PCR reactions were incubated for 35 cycles under cycling conditions of 94° C. for 30 sec, 70-56° C. for 1 min (starting at 70° C. and decreasing by 0.4° C. per cycle), and 72° C. for 1-5 min, depending on the size of the expected PCR product. As a final step the reaction mixture was incubated for 7 min at 72° C. Reaction products were analyzed by polyacrylamide slab gel electrophoresis and ethidium bromide staining.

Molecular Cloning of Viral cDNA and Preparation of Plasmid DNA

PCR products representing EAV-specific cDNA sequences were subjected to restriction endonuclease treatment and restriction fragments were purified using preparative low melting point agarose gel electrophoresis. Specific DNA bands were extracted from the gel by a hot phenol procedure followed by gel filtration. Restricted and purified EAV cDNA was inserted into the pCR3.1 mammalian expression vector (Invitrogen catalogue no. K3001-01, Chatsworth, Calif.). This 5044 nucleotide (nt) long mammalian vector designed for high-level constitutive expression contains a putative transcriptional start site (620-625 nt), a T7 promoter/priming site (638-657 nt), a multiple cloning site (670-785 nt), and a reverse priming site (796-815 nt). Vector plasmids were prepared using restriction endonucleases and purified as described above. In addition, restricted vector DNA was dephosphorylated using calf intestine phosphatase (CIP). Ligation of specific EAV cDNA fragments with expression vector DNA was performed as described previously (Rösen-Wolff et al., 1991, Identification and mapping of the UL56 gene transcript of herpes simplex virus type 1. Virus Res. 19, 115-126). The resulting recombinant plasmid construct for vaccination is listed in TABLE 2. The specificity of the reaction products was confirmed by nucleotide sequence analysis of the insert and flanking vector regions. Construction of plasmid expressing equine interleukin 2: total cell RNA of horse lymphocytes was prepared using the guanidinium isothiocyanate/cesium chloride procedure as described previously (Tobiasch et. al., 2000).

PCR products and/or synthetic cDNA sequences of the translation unit of equine IL-2 were subjected to restriction endonuclease treatment (BamHI and EcoRI) and restriction fragments were extracted from the gel by a hot-phenol procedure followed by gel filtration. Purified cDNA of equine IL-2 was inserted into the corresponding recognition sites of restriction endonucleases BamHI and EcoRI of recombinant plasmid pAT153 (GeneBank accession number: L08853). The mammalian expression vector pCR3.1 (Invitrogen) was prepared using restriction endonucleases BamHI and EcoRI and purified as described above. The molecular cloning of specific equine IL-2 fragments with expression vector DNA, the amplification, extraction and purification of the recombinant plasmid was performed as described previously (Tobiasch et. al., 2000).

Nucleotide Sequence Analysis

PCR products were treated with 5 vol phenol:1 vol chloroform (=5:1) and precipitated with 3 vol 95% ethanol containing 100 mM sodium acetate. The DNA was then washed with 70% ethanol and dissolved in bi-distilled water to a final concentration of 20 ng/µl. Plasmid DNA was prepared using the Qiagen tip100 Kit (Qiagen, Hilden, Germany) according to the instructions of the manufacturer. Purified DNA was adjusted in $H_2O$ to a final concentration of 1 µg/µl. Purified DNA was automatically sequenced with a 373A "Extended" DNA sequencer using the BigDye Terminator-Taq cycle sequencing technique (Applied Biosystems GmbH, Weiterstadt, Germany). Each sequencing reaction was performed in a volume of 20 µl containing 100 ng of a PCR product or 0.5 µg of plasmid DNA, 50 pmol of the sequencing primer, and 5 µl of the BigDye Terminator reaction mixture. The cycle sequencing reaction was incubated for 28 cycles in an automated temperature cycling reactor (GeneE, Techne, Cambridge, UK) under cycling conditions of 96° C. for 30 sec and 60° C. for 4 min per cycle. The samples were prepared for electrophoresis as described by the manufacturer. The electrophoresis of the samples was carried out on a 36-well 48-cm WTR (well to read) polyacrylamide gel. The nucleotide sequences obtained from individual sequencing reactions were assembled using the Sequence Navigator software (version 2.1, Applied Biosystems GmbH, Weiterstadt, Germany). Nucleotide and amino acid sequences were compared to current GenBank, EMBL, and SwissProt database sequence entries using the BLAST service of the National Center for Biotechnology Information (National Library of Medicine, Bethesda, Md., USA). Physio-chemical properties of proteins were determined and conserved sequence motifs were identified with the PHYSCHEM and PROSITE programs included in the PC/Gene software (release 6.85, A. Bairoch, University of Geneva, Switzerland). The ClustalX program (version 1.64b) (Thompson et al., 1997, The CLUSTAL_X windows interface: flexible strategies for multiple sequence alignment aided by quality analysis tools. Nucleic Acids Res. 25, 4876-4882) was used to generate multiple sequence alignments.

Preparation of Viral RNA and Northern Blot Analysis

Total cellular RNA was isolated at different times after infection using the guanidium/cesium chloride method as described previously (Rösen-Wolff et al., 1988, Comparative analysis of the transcripts mapped in the BamHI DNA fragment B of avirulent HSV-1 HFEM, virulent HSV-1 F, and their intratypic recombinant viruses. Virus Res. 10, 315-324; Rösen-Wolff et al., 1989, Organotropism of latent herpes simplex virus type 1 is correlated to the presence of a 1.5 kb RNA transcript mapped within the BamHI DNA fragment B (0.738 to 0.809 map units), Virus Res. 12, 43-52; and Rösen-Wolff and Darai, 1991). The Northern blot analyses of these RNAs were carried out using formaldehyde agarose gel (1%) electrophoresis as described elsewhere (Rösen-Wolff et al., 1988; Rösen-Wolff et al., 1989; Rösen-Wolff and Darai, 1991).

Serum Neutralization Test

Neutralization tests (NT) were carried out by diluting EAV-specific mouse or rabbit sera with PBS (1:2 to 1:1024) in a Falcon microtiter plate. Serum dilutions (50 µl) were mixed with 100 TCID$_{50}$ of EAV (50 µl). The serum-virus mixture was incubated in a 5% $CO_2$-air atmosphere at 37° C. for 2 h. Subsequently, 5×10$^3$ RK13 cells in suspension were added to each sample of the serum-virus mixture. After 12 h, the infected cultures were overlaid with BME containing 10% FCS and 0.5% carboxymethylcellulose. Then the cultures were incubated for 3-4 days at 37° C. in a 5% $CO_2$-air atmosphere. Titers of infectious units were determined after staining with 1% crystal violet.

Immunoblot Analysis

Confluent monolayers of cells were harvested by scraping the cells from the culture well, petri dishes, and/or flasks after being washed three times with PBS (pH 7.2). The final cell pellet was resuspended in distilled water. Protein concentration was measured under the standard method (Bradford, 1976). Samples were dissolved in an equal volume of lysis buffer (0.01 M Tris HCl, 10% glycerol, 2% SDS, 5% β-mercaptoethanol, 0.1% (w/v) bromophenol blue, pH 8), heated for five minutes at 95° C., and subjected to SDS-PAGE according to the method of Laemmeli (1970). Proteins derived from infected and transfectant cells, as well as recombinant N protein were separated by SDS-PAGE and electroblotted onto nitrocellulose filters using semi-dry electroblotting chambers (Renner, Darmstadt, Germany). Transfer efficiency was monitored by Ponceau staining (Sigma, Munich, Germany). Filters were blocked for 1 h and incubated with a 1:1000 and 1:2000 dilution of the rabbit antisera mentioned above. Alkaline phosphatase conjugated antibodies (anti rabbit or mouse Ig-AP, Boehringer Mannheim, Germany) were used to detect interaction of the rabbit or mouse antiserum with EAV protein.

Enzyme Linked Immunosorbent Assay (ELISA)

Polysorb F8 Microtiter Plates (Nunc, Wiesbaden, Deutschland) were coated with 50 µl EAV Protein (EAV+Host (RK13)) at a concentration of 2 µgxml$^{-1}$ in PBS (+0.05% $N_3Na$) over night at room temperature, followed by three cycles of washing with $H_2O$ and then post-coated with 300 µl Blocking Buffer (0.017 M $Na_2B_4O_7$×10$H_2O$, 0.12 M NaCl, 0.05% Tween 20, 1 mM EDTA, 5% BSA, 0.05% $NaN_3$) for 3 h at 28° C. followed by three cycles of washing with $H_2O$.

For the assay, the following reagents were successively used: rabbit anti-EAV serum at a reciprocal dilution up to 16000 or mouse anti-EAV serum at a reciprocal dilution up to 800. The dilutions were made in Sample buffer POD (DADE Behring, Marburg, Deutschland). After three cycles of washing with 300 µl/well, horse-radish peroxidase labeled rabbit-anti IgG second antibody or the horse-radish peroxidase labeled mouse-anti IgG second antibody (Boehringer, Mannheim, Deutschland) at a predetermined optimum dilution of 1:3000 each was added. The dilutions were made in blocking buffer. Incubation steps were done for 1 h at 28° C., each followed by three cycles of washing with 300 µl/well Washing Buffer (DADE Behring, Marburg, Deutschland). Color was developed by adding 200 µl/well of freshly prepared Buffer/Substrate TMB and Chromogen TMB (10:1) (DADE Behring, Marburg, Deutschland). The assay was stopped after 30 min by the addition of 50 µl/well Stopping Solution POD (DADE Behring, Marburg, Deutschland) and read according to standard procedures at 450 nm on an automatic ELISA reader (MR5000, DYNATECH, Denkendorf, Deutschland).

Computer-Assisted Sequence Analysis

Nucleotide sequences were compiled using the ABI sequence navigator software version 1.2. Nucleotide and amino acid sequences were analyzed using the PC/GENE program release 6.85 (Intelligenetics Inc. Mountain View, Calif., U.S.A.) and OMIGA program release 11.3 (Oxford Molecular Group Ltd., Oxford, UK).

Results

Establishment of a Cell Culture System for Virus Propagation, Isolation of Virus Particles, and Extraction of Viral RNA The EAV used in this study was grown and propagated on rabbit kidney cells (RK-13). Virions of EAV were prepared, purified, and the viral RNA was extracted.

Generation of Specific Rabbit Antisera Against Whole Virus

In order to specifically detect viral gene products by serological assays a polyclonal hyperimmune rabbit antiserum was raised against complete EAV virion components in New Zealand white rabbits. The protocol of an exemplary immunization experiment is shown in TABLE 1. The titer of the antiserum was found to be >1:2000 as determined by Western Blot analysis.

TABLE 1

An exemplary experimental protocol used for the production of polyclonal antibodies against EAV in New Zealand white rabbit is illustrated below:

| DATE | TREATMENT |
| --- | --- |
| 09.06.1998 | Premium-serum |
|  | 10 × 620 µl |
| 10.06.1998 | 1$^{st}$ inoculation* |
|  | 0.5 ml/s.c. |
| 24.06.1998 | 2$^{nd}$ inoculation* |
|  | 0.5 ml/s.c. |
| 08.07.1998 | 3$^{rd}$ inoculation* |
|  | 0.5 ml/s.c. |
| 22.07.1998 | 4$^{th}$ inoculation* |
|  | 0.5 ml/s.c. |
|  | First bleeding (10 ml) |
|  | Titer by immunoblot analysis = 1:200 |
| 30.07.1998 | 5$^{th}$ inoculation* |
|  | 0.5 ml/s.c. |
| 11.08.1998 | Final bleeding (30 × 1.5 ml) |
|  | Titer by immunoblot analysis = >1:2000 |

Virus: EAV in 0.5 ml PBS, purified by sucrose gradient centrifugation
Animal: New Zealand white rabbit (2 kg/female)

TABLE 2

Properties of the constructed mammalian expression vector harboring the EAV-specific ORF 2 cDNA of the individual translation units.

| Construct Name | EAV-Specific Insert (Nucleotide Position) | Expression Vector (Restriction Sites) | Oligonucleotide Primers |
|---|---|---|---|
| pCR3.1-EAV-02-Bx | ORF 2b: small glycoprotein, G$_s$ (SEQ ID NO: 2, at 9807-10490; Giese et. al., 2002) | pCR3.1 (BamHI/XbaI) G/GATCC/T/CTAGA | P-BamHI-EAV-02-F1 P-XbaI-EAV-02-R1n |

TABLE 3

Properties of the EAV-specific cDNA obtained by long range

TABLE 6

Sample collection and immunization strategy

| IMMUNIZATION STAGE | DNA APPLICATION | COLLECTION OF PLASMA SAMPLES | ISOLATION OF PBMC* |
|---|---|---|---|
| Pre-immunization | n.d. | Sep. 24, 2001 | Sep. 24, 2001 |
| Basic immunization | Oct. 02, 2001 | n.d. | n.d. |
| 1. Booster | 30-10-2001 | Nov. 02, 2001 | Nov. 02, 2001 |
| 2. Booster | Nov. 28, 2001 | Nov. 27, 2001 | Nov. 27, 2001 |
| | | Dec. 06, 2001 | Dec. 06, 2001 |
| | | Dec. 27, 2001 | Dec. 27, 2001 |
| | | Feb. 04, 2002 | |
| | | Feb. 27, 2002 | |
| | | Mar. 26, 2002 | |
| | | Apr. 20, 2002 | |
| | | May 29, 2002 | |

*peripheral blood mononuclear cells
n.d.: not done

TABLE 7

Results of neutralization tests (NT) in which sera of two horses, Horse 1 (Maisje) and Horse 2 (Rudi), were screened for the detection of neutralizing antibodies against EAV following DNA vaccination with cDNA of EAV-ORF 2 and equine interleukin 2 (IL-2). Serum samples for detecting neutralizing antibodies were taken prior to vaccination and at 4-5 week intervals thereafter until 8 months post vaccination. TABLE 7 shows that both horses responded to immunization with EAV-ORF 2, although Horse 1 developed a stronger cellular immunity. The production of antibodies started at 4-8 weeks after initial immunization and reached maximal levels 4 weeks after the second booster injection. Four weeks after immunization, no antibodies could be detected in either animal. However, after 12 weeks, a significant production rate was still measureable in both animals. Surprisingly, even after 34 weeks, neutralizing antibodies at a high titer were maintained in the vaccinated horses. Of great interest is the observation that both horses produced a comparable amount of antibodies, despite the significant difference in the horse age.

| IMMUNIZATION SCHEDULE: | NT-Titer: | |
|---|---|---|
| | Horse 1 (Maisje) | Horse 2 (Rudi) |
| Pre-Vaccination Control, Co-serum | <1:2 | <1:2 |
| Post-vaccination (PV) | | |
| 1. PV-serum: 4 weeks | <1:2 | <1:2 |
| 2. PV-serum: 8 weeks | 1:32 | 1:96 |
| 4. PV-serum: 12 weeks | 1:128 | 1:128 |
| 5. PV-serum: 18 weeks | 1:128 | 1:128 |
| 6. PV-serum: 21 weeks | 1:128 | 1:128 |
| 7. PV-serum: 25 weeks | 1:64 | 1:96 |
| 8. PV-serum: 30 weeks | 1:128 | 1:32 |
| 9. PV-serum: 34 weeks | 1:128 | 1:96 |

Co-Serum: Control serum prior to vaccination
PV-serum: Post-vaccination serum after vaccination Cytotoxic T-Cell Reactions of the Horses Against EAV after DNA Vaccination The immunological methods are mostly based on standard protocols of Current Protocols in Immunology (1997) and modifications of published protocols (Allen et al.; J. Virol. 1995, 69, 606-612; Niewiesk et al., J. Virol. 1993, 67, 75-83; Baker et al., J. Immunol. 1999, 162, 4496-4501).

Target Cell Isolation:

Autologous mononuclear blood cells were isolated from fresh blood prior vaccination and purified via Percoll gradient (60% v/v, Pharmacia) centrifugation. Cells within the visible band were collected, and were cryopreserved in liquid nitrogen at a concentration of $2-5 \times 10^6$ cells/ml in a cryomedium (45% RPMI 1640, 45 FCS, 10% DMSO) until use in the CTL assays. Controls were prepared from blood specimens obtained prior to vaccination.

Antigen Specific Stimulation:

The autologous mononuclear cells were irradiated at 300 Gy Cobalt and were incubated with EAV at a M.O.I. (multiplicity of infection) of 1 for four hours/37° C. and immediately mixed with non-irradiated lymphocytes (effector cells). $3 \times 10^6$ irradiated stimulator cells and $1 \times 10^7$ non-irradiated responder cells were used for stimulation.

Activation was supported by IL-2, 5 µg ConcanavalinA (ConA) or 3 µg Pokeweed-Mitogen (PWM)/$10^7$ cells. The activated effector T-lymphocytes were isolated by Percoll gradient (60%) after five to six days of co-cultivation together with the stimulator cells.

Chromium-Release-Assay:

Target cells were infected with EAV at a M.O.I. of 10 overnight.

The cells were then incubated with 3.7 MBq Na$^{51}$CrO$_4$ (Amersham, Piscataway, N J, USA)/$10^6$ cells/37° C./90 min. After two washing steps with PBS (400×g/22° C./5 min) $10^4$ target cells/50 µl/well were plated on a microtiter plate. Effector cells were added at different ratios (E:T ratio as indicated in TABLES 8 and 9). An aliquot of stimulator cells was taken in order to measure the uptake of $^{51}$Cr (0.3-2.2 cpm/cell). The spontaneous release of $^{51}$Cr and the maximum release (total release, induced by the addition of 2.5% Triton X-100) was determined by triplicate measurements in each TEST.

The activated T-lymphocytes (CTLs), effector cells, were added to the $^{51}$Cr labeled target cells, the microtiter plates were centrifuged (150×g/22° C./2 min) and then incubated (37° C./5% CO$_2$/6 hr). Tests were performed in duplicate.

The cells were then centrifuged (600×g/5 min), and the released radioactivity in 75 ml supernatant was measured using a gamma counter (Wallac 1450).

Calculation of Cell-Lysis

The specific lysis of the target cells were calculated according to the following standard formula:

$$\text{Specific lysis } (\%) = (a-b)/(c-b) \times 100$$

a: release/cpm in wells containing combined effector and target cells b: spontaneous release/cpm from the target cells c: maximum release/cpm from the target cells The spontaneous release (b) was in the range of 37+/−6%.

The maximum of release (c) was of in the range of 95+/−3%.

The Student T-test was used for calculation of the specific lysis.

Figure 2:
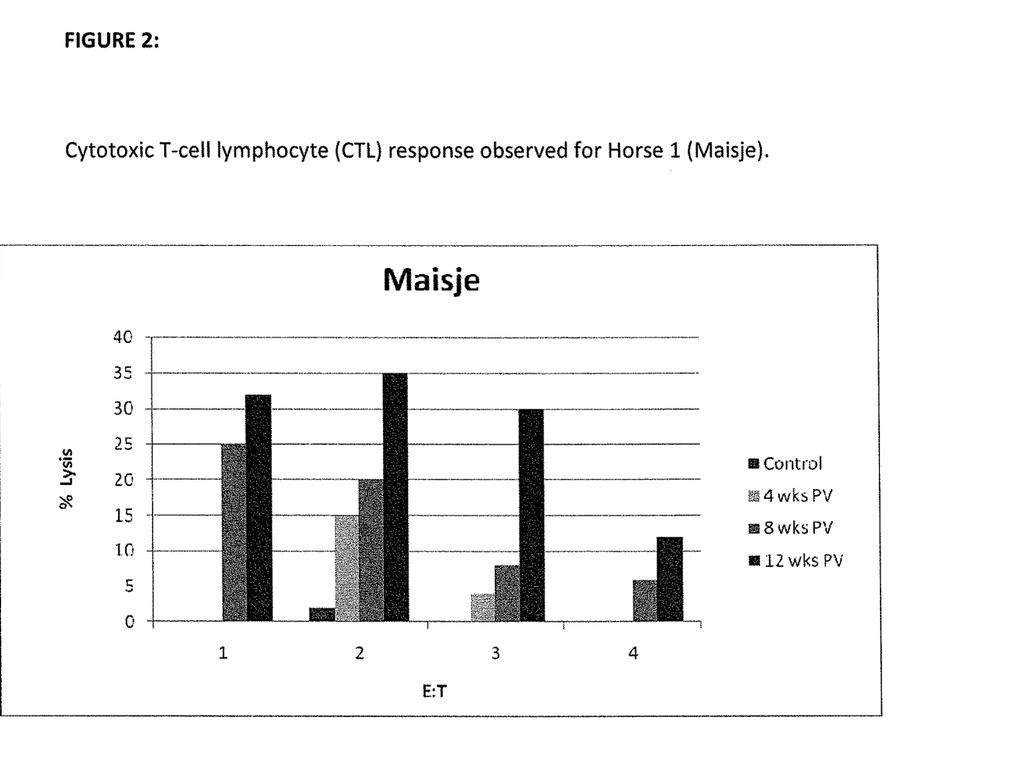
FIG. 2
Cytotoxic T lymphocyte (CTL) response in peripheral blood lymphocytes of Horse 1 at different effector-to-target (E:T) ratios as indicated. Controls depict specific lysis in pre-vaccine lymphocytes; PV refers to post-vaccination lysis.
Figure 3:
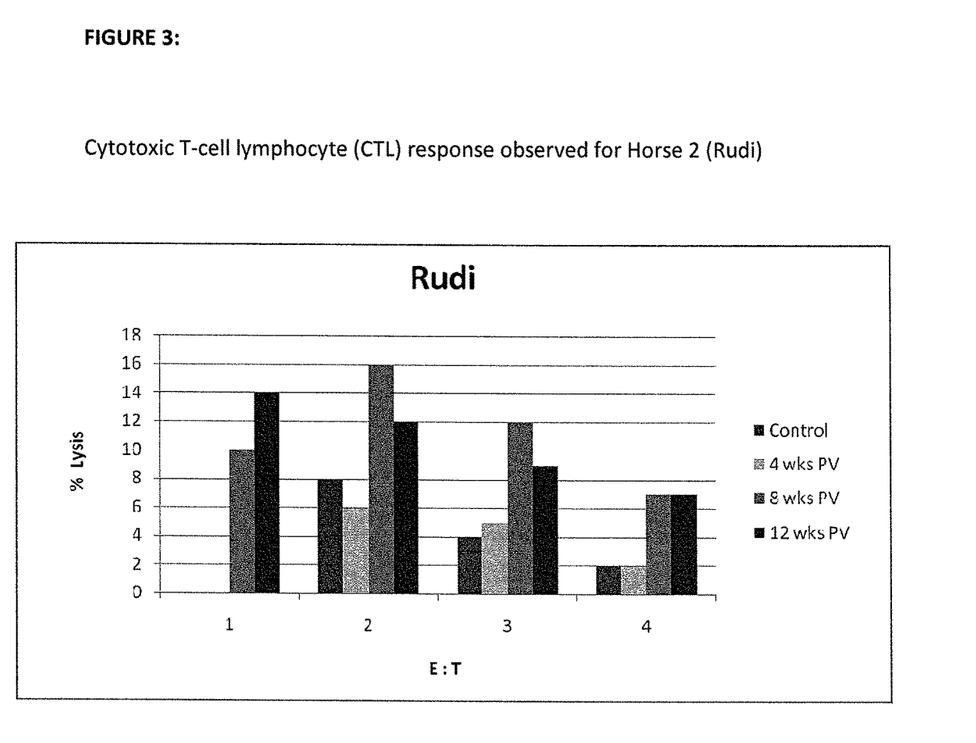
FIG. 3
CTL response in peripheral blood lymphocytes of Horse 2 at different effector-to-target (E:T) ratios as indicated. Controls depict specific lysis in pre-vaccine lymphocytes; PV refers to post-vaccination lysis.

The results of the cytotoxic T-cell reactions of Horse 1 and Horse 2 against EAV after DNA vaccination are shown for each horse in TABLES 8 and 9 (specific lysis values) and in FIGS. 2 and 3 (time post-vaccination), respectively.

TABLE 8

Cytotoxic T-cell reactions of Horse 1 (MAISJE)

| HORSE 1 (MAISJE) | Effector Cell:Target Cell (E:T) at a ratio of 1: | 1. TEST: (in cpm) | 2. TEST: (in cpm) | 3. TEST: (in cpm) | 4. TEST: (in cpm) |
|---|---|---|---|---|---|
| | 100 | — | — | 25 | 32 |
| | 50 | 2 | 15 | 20 | 35 |
| | 25 | 0 | 4 | 8 | 30 |
| | 12.5 | 0 | 0 | 6 | 12 |

FIG. 2 illustrates the cytotoxic T-cell Lymphocyte (CTL) response in peripheral blood lymphocytes observed in Horse 1 (Maisje) at different effector-to-target ratios as indicated. Controls depict specific lysis in pre-vaccine lymphocytes; PV=post-vaccination. Horse 1 developed a strong cellular immunity following vaccination with EAV-ORF 2. As early as 4 weeks post-vaccination (PV), a rise of the EAV-specific CTL activity increased to 20% specific lysis of chromated target cells compared to the control value of 2%. Maximum CTL response was reached at 8 weeks post-immunization, wherein this response was sustained at 35% specific lysis even after 12 weeks following vaccination.

TABLE 9

Cytotoxic T-cell reactions of Horse 2 (RUDI)

| HORSE 2 (RUDI) | Effector Cell:Target Cell (E:T) at a ratio of 1: | 1. TEST: (in cpm) | 2. TEST: (in cpm) | 3. TEST: (in cpm) | 4. TEST: (in cpm) |
|---|---|---|---|---|---|
| | 100 | — | — | 10 | 14 |
| | 50 | 8 | 6 | 16 | 12 |
| | 25 | 4 | 5 | 12 | 9 |
| | 12.5 | 2 | 2 | 7 | 7 |

FIG. 3 illustrates the cytotoxic T-cell Lymphocyte response in peripheral blood lymphocytes observed in Horse 2 (Rudy) at different effector-to-target ratios as indicated. Controls depict specific lysis in pre-vaccine lymphocytes; PV=post-vaccination. Horse 2 developed a significant cellular immunity against the EAV 2 antigen. However, the overall CTL response was weaker than that observed in Horse 1 perhaps since older hosts are typically able to react to a DNA vaccine in a comparably successful manner than younger subjects. Although, it must be emphasized that the subject's age did not influence the animal's overall ability to induce a humoral or cellular immune response. Maximum specific lysis was 16%, observed at 8 weeks following vaccination.

Generally, the results using the EAV vaccine containing exclusively ORF 2 sequences are significant as both of the tested horses developed neutralizing antibodies that were detectable and sustainable over a period of at least eight months, and both equine subject demonstrated an EAV-specific specific CTL immune response.

The invention claimed is:

1. A nucleic acid vaccine composition that is protective against the Arteriviridae family and induces a cellular immune response, said vaccine encodes only one equine arteritis virus (EAV) protein consisting of open reading frame (ORF) 2 or 2b, wherein the coding sequence for ORF 2 or 2b is SEQ ID NO:1 or SEQ ID NO:2, wherein said vaccine composition is administered as a single base immunization without a booster, or as a base immunization followed by a first boost after 8-12 weeks, or as a base immunization followed by a first boost after 8-12 weeks and a second boost after 12 months.

2. The vaccine composition according to claim 1, wherein said nucleic acid is cDNA.

3. The vaccine composition according to claim 1, wherein said vaccine composition comprises one or several nucleic acid vectors each encoding the EAV sequence of claim 1.

4. The vaccine composition according to claim 3, wherein said nucleic acid vector(s) is/are expression vector(s).

5. The vaccine composition according to claim 4, wherein said expression vector(s) comprise(s) a eukaryotic cis-acting transcription/translation sequence functionally linked to the EAV sequence(s).

6. The vaccine composition according to claim 5, wherein said expression vector(s) is/are selected from the group of pCR3.1, pcDNA3.I/His A, pcDNA3.1/His B, pcDNA3.1/His C, and pDisplay (pD).

7. The vaccine composition according to claim 1, further comprising a nucleic acid encoding interleukin 2(IL-2) or a vector or expression vector comprising said nucleic acid encoding IL-2.

8. The vaccine composition according to claim 1, further comprising a pharmaceutically acceptable carrier or excipient.

9. The vaccine composition according to claim 1, further comprising one or several adjuvants selected from the group of Muramyl Dipeptide (MDP), Montanide 720, Poly Inosine:

Cytosine (Poly I:C) or plasmid DNA comprising unmethylated cytosine, guanine dinucleotide sequence motifs (CpG).

10. The vaccine composition according to claim 1, further comprising:
   (a) an expression vector comprising a nucleic acid encoding IL-2; and
   (b) a carrier, an excipient or an adjuvant.

11. The vaccine composition according to claim 1, wherein the nucleic acid is encapsulated into cationic liposomes.

12. A method for prevention and/or treatment of EAV infection in a horse, comprising injecting a vaccine composition according to claim 1 into muscular cells of the horse in vivo; inducing a protective or therapeutic immune response in said horse upon or after exposure to EAV; and monitoring the reduction of EAV-associated symptoms or the reduction of horizontal or vertical transmission.

13. The method of claim 12, further comprising: coating the vaccine composition onto carrier particles; and accelerating the coated carrier particles into epidermal cells of the horse in vivo.

14. A kit comprising a vaccine composition according to claim 1 which is protective and/or therapeutic against infections mediated by an *Arteriviridae* virus in an animal, wherein said vaccine composition or one or more nucleic acid vector(s) induces a protective and/or therapeutic immune response following administration as a single base immunization without a booster, or as a base immunization followed by a first boost after 8-12 weeks, or as a base immunization followed by a first boost after 8-12 weeks and a second boost after 12 months.

15. The kit according to claim 14, wherein said *Arteriviridae* virus is selected from the group consisting of equine arteritis virus (EAV), porcine reproductive and respiratory syndrome virus (PRRSV), and simian haemorrhagic fever virus (SHFV).

* * * * *